United States Patent [19]

Sucrow et al.

[11] Patent Number: 4,537,698
[45] Date of Patent: Aug. 27, 1985

[54] LIQUID CRYSTALLINE PIPERIDINE DERIVATIVES

[75] Inventors: Wolfgang Sucrow; Wolfgang Schatull, both of Paderborn; Peter Fuss, Mühltal-Traisa, all of Fed. Rep. of Germany

[73] Assignee: Merck Patent Gesellschaft mit beschränkter Haftung, Darmstadt, Fed. Rep. of Germany

[21] Appl. No.: 499,685

[22] Filed: May 31, 1983

[30] Foreign Application Priority Data

May 28, 1982 [DE] Fed. Rep. of Germany ....... 3220155

[51] Int. Cl.³ .................... C09K 3/34; G02F 1/13; C07D 211/08; C07D 211/62; C07D 211/38; C07D 211/20; C07D 211/14
[52] U.S. Cl. .................... 252/299.61; 252/299.5; 350/350 R; 350/350 S; 546/192; 546/207; 546/215; 546/216; 546/217; 546/218; 546/221; 546/225; 546/227; 546/228; 546/230; 546/232; 546/238; 546/235; 546/239
[58] Field of Search .................... 350/350 R, 350 S; 252/299.61, 299.5; 546/192, 207, 215, 216, 217, 218, 221, 225, 227, 228, 230, 232, 238, 239, 235

[56] References Cited

U.S. PATENT DOCUMENTS

| | | | |
|---|---|---|---|
| 3,314,952 | 4/1967 | Robinson | 546/192 |
| 3,392,171 | 7/1968 | Fonken et al. | 546/192 |
| 3,960,961 | 6/1976 | Lednicer | 546/192 |
| 4,349,452 | 9/1982 | Osman et al. | 252/299.61 |

FOREIGN PATENT DOCUMENTS

| | | | |
|---|---|---|---|
| 19665 | 12/1980 | European Pat. Off. | 252/299.61 |
| 1311580 | 3/1973 | United Kingdom | 546/192 |

OTHER PUBLICATIONS

Karamysheva, L. A. et al., Advances in Liq. Cryst. Res. & Applications, Bata, L., Pergamon Press, Oxford, pp. 997–1002, (1980).
C.A., vol. 82, 72751m, (1975).
C.A., vol. 67, 72251p, (1967).

*Primary Examiner*—Teddy S. Gron
*Attorney, Agent, or Firm*—Millen & White

[57] ABSTRACT

New piperidine derivatives

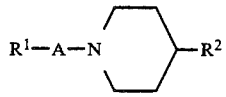

in which
$R^1$ and $R^2$ each independently is alkyl or alkoxy each of 1 to 10 C atoms, —Y—Z, F, Cl, Br or CN, and the radical $R^1$ can also be H,
Y is —CO—O—, —O—CO or a single bond,
Z is —Q—$R^3$ or alkyl having 1–10 C atoms,
Q is 1,4-phenylene or 1,4-cyclohexylene,
$R^3$ is alkyl having 1–10 C atoms, F or CN, and
A is 1,4-cyclohexylene or 1,3-dioxane-2,5-diyl, and their acid addition salts, can be used as components of dielectrics for electro-optical display elements.

10 Claims, No Drawings

LIQUID CRYSTALLINE PIPERIDINE DERIVATIVES

This invention relates to new liquid crystalline compounds

SUMMARY OF THE INVENTION

It is an object of this invention to provide new stable liquid crystalline or mesogenic compounds which are suitable for use as components of liquid crystalline dielectrics, in particular for nematic phases having a wide nematic range, low viscosity and/or small birefringence.

Upon further study of the specification and appended claims, further objects and advantages of this invention will become apparent to those skilled in the art.

These objects have been achieved by providing new piperidine derivatives of formula I

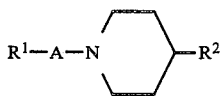
I in which $R^1$ and $R^2$ each independently are alkyl or alkoxy each of 1 to 10 C atoms, —Y—Z, F, Cl, Br or CN, and the radical $R^1$ also can be H, Y is —CO—O—, —O—CO or a single bond, Z is —Q—$R^3$ or alkyl of 1-10 C atoms, Q is 1,4-phenylene or 1,4-cyclohexylene, $R^3$ is alkyl of 1-10 C atoms, F or CN, and A is 1,4-cyclohexylene or 1,3-dioxane-2,5-diyl, and their acid addition salts.

These substances, like similar compounds which are disclosed in, for example, German Offenlegungsschrift 2,702,598 can be used as components of liquid crystalline dielectrics, in particular for displays which are based on the principle of the twisted cell.

It has been found that compounds of formula I are highly suitable for use as components of liquid crystalline dielectrics. In particular, they can be used to prepare stable liquid crystalline phases having a wide nematic range, low viscosity and small birefringence.

DETAILED DESCRIPTION

Compounds of formula I are distinguished by a small birefringence (low optical anisotropy) and by their polar character. Because of their low birefringence, they are of advantage in particular in the case of the twisted cell which has a particularly angle-independent contrast (compare German Offenlegungsschrift 3,022,818). By virtue of their polar character, they are particularly suitable for use as solvents or solubilizers, for example for dichroic dyestuffs (host for guest-host mixtures). Since they are bases, they combine with acids to give form-anisotropic salts; these give rise to an anisotropic (direction-dependent) conductivity, which is favorable for generating high-contrast dynamic scattering.

The provision of the compounds of formula I also, quite generally, considerably widens the range of liquid crystalline substances which, from various application-related aspects, are suitable for preparing nematic mixtures.

Compounds of formula I have many uses. Depending on the choice of substituents, these compounds can be used as base materials from which liquid crystalline dielectrics are predominantly composed; but compounds of formula I can also be added to liquid crystalline base materials for other compound classes, in order, for example, to reduce the viscosity or the birefringence of such dielectric materials. Compounds of formula I, in particular those which contain cyclohexane or dioxane rings having substituents in the cis configuration as well as those in which $R^1$ and/or $R^2$ are H, Cl, Br or CN, are also suitable for use as intermediates in preparing other substances, including other compounds of formula I, which can be used as components of liquid crystalline dielectrics.

Compounds of formula I are colorless in the pure state, and form liquid crystalline mesophases within a temperature range favorably located for electrooptical use. Chemically they are very stable.

The present invention thus relates to compounds of formula I and to a process for their preparation, comprising, treating a compound which otherwise is of formula I but which in place of hydrogen atoms contains one or more additional reducible groups and/or C—C bonds with a reducing agent, or to prepare esters of formula I ($R^1$ and/or $R^2$=—Y—Z), esterifying a corresponding carboxylic acid, or to prepare nitriles of formula I ($R^1$, $R^2$ and/or $R^3$=CN), dehydrating a corresponding carboxamide, or to prepare dioxane derivatives of formula I (A=1,3-dioxane-2,5-diyl), reacting a corresponding formyl compound or one of its reactive derivatives with a corresponding 1,3-diol, or optionally, treating a base of formula I with an acid and thus converting it into one of its acid addition salts, or optionally, treating an acid addition salt of a compound of formula I with a base to liberate the compound of formula I.

The present invention also relates to the use of compounds of formula I as components of liquid crystalline dielectrics. The invention moreover relates to liquid crystalline dielectrics containing at least one compound of formula I as well as to electro-optical display elements which contain such dielectrics.

Above and below, $R^1$, $R^2$, $R^3$, Y, Z, Q and A are as defined above unless expressly stated otherwise. Below, for smplicity, "Cy" is 1,4-cyclohexylene, "Dio" is 1,3-dioxane-2,5-diyl, "Phe" is 1,4-phenylene and "Pip" is piperidine-1,4-diyl. Thus, formula I can also be written in the form $R^1$-A-Pip-$R^2$.

The compounds of formula I encompass, for example, the preferred compounds of formula Ia

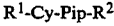
Ia and the compounds of formula Ib

Ib which formula embraces the 2-$R^1$-5-(Pip-$R^2$)-1,3-dioxanes and the 2-(Pip-$R^2$)-5-$R^1$-1,3-dioxanes.

Individual preferred groups of compounds of formula I also are the compounds of formulae Ic to In:

| | |
|---|---|
| Z—O—CO—A—Pip—$R^2$ | Ic |
| Z—CO—O—A—Pip—$R^2$ | Id |

| | |
|---|---|
| R¹—A—Pip—CO—O—Z | Ie |
| R¹—A—Pip—O—CO—Z | If |
| R¹—A—Pip—Y—Phe—R³ | Ig. |
| R¹—A—Pip—Y—Cy—R³ | Ih |
| R³—Phe—Y—A—Pip—R² | Ii |
| R³—Cy—Y—A—Pip—R² | Ij |
| R³—Phe—Y—A—Pip—Y—Phe—R³ | Ik |
| R³—Phe—Y—A—Pip—Y—Cy—R³ | Il |
| R³—Cy—Y—A—Pip—Y—Phe—R³ | Im |
| R³—Cy—Y—A—Pip—Y—Cy—R³ | In | where, in the formulae Ik to In, the two radicals R³ and the two radicals Y can each be identical or different from one another.

Of compounds of formula I and of formulae Ia to In, those stereoisomers are preferable in which the substituents on the 1,4-cyclohexylene radicals are in each case in the trans-position relative to each other.

In compounds of formula I and of formulae Ia to In, the alkyl or alkoxy radicals can be straight-chained and have 2, 3, 4, 5 or 6 C atoms, and accordingly they preferably are ethyl, propyl, butyl, pentyl, hexyl, ethoxy, propoxy, butoxy, pentyloxy or hexyloxy, and also methyl, heptyl, octyl, nonyl, decyl, methoxy, heptyloxy, octyloxy, nonyloxy or decyloxy.

Those compounds of formulae I and Ia to In which have branched "wing" groups, R¹, R² and/or R³, can occasionally be of importance, because of their superior solubility in the customary liquid crystalline base materials, but in particular as chiral dopants if they are optically active. Branched groups of this type contain, as a rule, not more than one chain branching. Preferred branched radicals R¹ and R² are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-heptyl (=1-methylhexyl), 2-octyl (=1-methylheptyl), 2-ethylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy or 1-methylheptyloxy.

Specifically, R¹ and R² preferably are alkyl, alkoxy or CN. Those compounds of formulae I and Ia to In are preferable in which at least one of the radicals contained therein has one of the specified preferred meanings. Particularly preferred, relatively small groups of compounds are those of formulae Io to Ir:

| | |
|---|---|
| NC—Cy—Pip—R² | Io |
| NC—Cy—Pip—Alkyl | Ip |
| Alkyl—Cy—Pip—Alkyl | Iq |
| Alkoxy—Cy—Pip—Alkyl | Ir |

Compounds of formulae I are prepared by methods known per se, which are described in the literature, (for example in standard works such as Houben-Weyl, Methoden der Organischen Chemie [Methods of Organic Chemistry], Georg-Thieme-Verlag, Stuttgart, which disclosure is incorporated by reference herein), under reaction conditions which are known and suitable for the reactions mentioned. It is also possible to use versions of these methods which are known per se but which are not specifically mentioned here.

The starting materials can, if desired, also be formed in situ, by leaving them in the reaction mixture and immediately reacting them further to give compounds of formula I.

Compounds of formula Ia are preferably prepared by producing an enamine of formula II

Enamines of formula II can be prepared, for example, by conventionally reacting known or readily preparable 4-R¹-cyclohexanones with known or readily preparable 4-R²-piperidines.

Enamines of formula II are preferably reduced by catalytic hydrogenation at temperatures of about 0° to about 200° under pressures of about 1 to 200 bar in an inert solvent, for example an alcohol, such as methanol, ethanol or isopropanol, an ether such as tetrahydrofuran (THF) or dioxane, an ester such as ethyl acetate, a carboxylic acid such as acetic acid or a hydrocarbon such as cyclohexane.

Preferred suitable catalysts are noble metals, such as Pt or Pd, which can be used in the form of oxides (for example $PtO_2$ or PdO), on a support (for example Pd on carbon, calcium carbonate or strontium carbonate) or in finely divided form (for example Pt black).

After the reduction stage, it can be preferable to separate any mixture of stereoisomers obtained into its components, for example by fractional crystallization of the hydrochlorides. As a rule, the hydrochlorides of the trans-isomers are left soluble.

Esters of the formula I (R¹ and/or R²=—Y—Z) can also be obtained by esterifying corresponding carboxylic acids of the formulae HOOC—A—Pip—R², R¹—A—Pip—COOH or Z—COOH (or their reactive derivatives) with alcohols or phenols of the formulae Z—OH, HO—A—Pip—R² or R¹—A—Pip—OH (or their reactive derivatives). Such starting materials can be prepared by methods analogous to those disclosed above using the compounds of formula II except wherein R¹ or R² are OH or COOH. These can be conventionally prepared, e.g., from the mentioned other compounds of formula II wherein one of R¹ or R², respectively, is Cl, or Br or, alternatively, CN to yield by hydrolysis the alcohols or, alternatively, the carboxylic acids.

Suitable reactive derivatives of the carboxylic acids mentioned are, in particular, the acid halides, especially the chlorides and bromides, and also the anhydrides, for example the mixed anhydrides of the formulae $CH_3CO$—O—OC—A—Pip—R², R¹—A—Pip13 CO—O—$COCH_3$ or Z—CO—O—$COCH_3$, azides or esters, in particular alkyl esters having 1-4 C atoms in the alkyl group.

Suitable reactive derivatives of the mentioned alcohols or phenols are, in particular, the corresponding metal alcoholates or phenolates of the formulae Z—OM, MO—A—Pip—R² or R¹—A—Pip—OM where M is one equivalent of a metal, preferably of an alkali metal, such as Na or K.

The esterification is preferably carried out in the presence of an inert solvent. Highly suitable are, in particular, ethers such as diethyl ether, di-n-butyl ether, THF, dioxane or anisole, ketones such as acetone, butanone or cyclohexanone, amides such as DMF or phosphoric hexamethyltriamide, hydrocarbons such as benzene, toluene or xylene, halogenohydrocarbons such as carbon tetrachloride or tetrachloroethylene, or sulfoxides such as dimethyl sulfoxide or sulfolane. Water-immiscible solvents can advantageously be used simultaneously to remove the water formed in the esterification by azeotropic distillation. In some cases, it is also possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually $-50°$ to $+250°$, preferably $-20°$ to $+80°$. At these temperatures, the esterification reactions are, as a rule, complete after 15 minutes to 48 hours.

The reaction conditions for the esterification largely depend, in particular, on the nature of the starting materials used. For instance, a free carboxylic acid is, as a rule, reacted with a free alcohol or phenol in the presence of a strong base, for example a mineral acid such as hydrochloric or sulfuric acid. A preferred method comprises reacting an acid anhydride or, in particular, an acid chloride with an alcohol, preferably in a basic medium. In particular, the following compounds are of importance for use as bases: alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline earth metal hydroxides, such as calcium hydroxide, or organice bases such as triethylamine, pyridine, lutidine, collidine or quinoline. In another preferred embodiment of the esterification, the alcohol or the phenol is first converted into the sodium or potassium alcoholate or phenolate, for example by treating the alcohol or phenol with ethanolic sodium hydroxide or potassium hydroxide solution, the alcoholate or phenolate is isolated and suspended, with stirring, together with sodium hydrogencarbonate or potassium carbonate in acetone or diethyl ether, and to this suspension is added a solution of the acid chloride or anhydride in diethyl ether, acetone of DMF, preferably at temperatures of about $-25°$ to $+20°$.

The nitriles of formula I, in particular those of the formulae Io and Ip, can be prepared by dehydrating the corresponding acid amides, for examples those of the formulae $H_2N—CO—A—Pip—R^2$ or $R^1—A—Pip—CONH_2$. The amides can be obtained, for example, from the corresponding esters or acid halides by reacting these with ammonia. Examples of suitable water-eliminating agents include inorganic acid chlorides such as $SOCl_2$, $PCl_3$, $POCl_3$, $PCl_5$, $SO_2Cl_2$, $COCl_2$, and also $P_2O_5$, $P_2S_5$ or $AlCl_3$ (for example in the form of a double compound with NaCl), aromatic sulfonic acids and sulfonyl halides. The dehydration can also be carried out in the presence or or absence of an inert solvent at temperatures of about 0° to 150°; examples of possible solvents include bases such as pyridine or triethylamine, aromatic hydrocarbons such as benzene, toluene or xylene, and amides such as DMF.

Dioxane derivatives of formula Ib are preferably prepared by reacting a corresponding formyl compound of the formula $R^1—CHO$ or $OCH—Pip—R^2$ (or one of its reactive derivatives) with a corresponding 1,3-diol of the formula $(HOCH_2)_2CH—Pip—R^2$ or $R^1CH(CH_2OH)_2$ (or with one of its reactive derivatives) preferably in the presence of an inert solvent such as benzene or toluene and/or of a catalyst, for example a strong acid such as sulfuric acid or benzenesulfonic of p-toluenesulfonic acid, at temperatures of about 20° to 150°, preferably 80° to 120°, °C. Suitable reactive derivatives of the starting materials include, primarily, acetals of the formulae $R^1—CH(OR^4)_2$, $(R^4O)_2CH—Pip—R^2$, $R^5—CH(OCH_2)_2CH—Pip—R^2$ or $R^1—CH(CH_2O)_2—CH—R^5$, in which $R^4$ is alkyl having 1–4 C atoms, two radicals $R^4$ together are also alkylene having 2 or 3 C atoms, and $R^5$ is H, alkyl having 1–4 C atoms or phenyl.

Some of the formyl compounds and 1,3-diols mentioned, as well as some of their reactive derivatives, are known, and the others can be straight-forwardly derived by standard methods of organic chemistry from compounds described in the literature. For example, the aldehydes of the formula $R^1—CHO$ can be prepared by oxidizing the corresponding alcohols or by reducing the corresponding carboxylic acids or their derivatives; the formylpiperidines of the formula $OCH—Pip—R^2$ can be prepared by formylating the corresponding piperidines; and the diols can be obtained by reducing the corresponding diesters of the formulae $(AlkylOOC)_2CH—Pip—R^2$ or $R^1—CH(COOAlkyl)_2$.

A base of formula I can be combined with an acid to give the corresponding acid addition salt. This reaction can be carried out with inorganic acids, for example sulfuric acid, nitric acid, hydrohalic acids, such as hydrochloric acid or hydrobromic acid, phosphorous-based acids, such as orthophosphoric acid, or sulfamic acid, or with organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic or naphthalenedisulfonic acid, or laurylsulfuric acid.

Conversely, it is possible to treat an acid addition salt of a compound of formula I with a base, for example with a strong inorganic base such as KOH or NaOH, to liberate the base of formula I.

Dielectrics according to this invention comprise 2 to 15, preferably 3 to 12, components of which at least one is a compound of formula I. The other components are preferably selected from among nematic or nematogenic substances, in particular from among the known such substances of the azoxybenzene, benzylideneaniline, biphenyl, terphenyl, phenyl, or cyclohexyl benzoate, phenyl or cyclohexyl cyclohexanecarboxylate, phenylcyclohexane, cyclohexylbiphenyl, cyclohexylcyclohexane, cyclohexylnaphthalene, 1,4-bis-cyclohexylbenzene, 4,4'-biscyclohexylbiphenyl, phenylpyrimidine, cyclohexylpyrimidine, phenyldioxane, cyclohexyldioxane, optionally halogenated stilbene, benzyl phenyl ether, tolane or substituted cinnamic acid classes.

The most important compounds suitable for use as components of such liquid crystalline dielectrics can be characterized by formula III $R^6$-D-G-E-$R^7$  III in which D and E each are a carboxylic or heterocyclic ring system selected from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene and tetrahydronaphthalene, quinazoline and tetrahydroquinazoline,

| G is | —CH=CH— | —N(O)=N— |
|---|---|---|
|  | —CH=CX— | —CH=N(O)— |
|  | —C≡C— | —CH$_2$—CH$_2$— |
|  | —CO—O— | —CH$_2$—O— |
|  | —CO—S— | —CH$_2$—S— |
|  | —CH=N— | —COO—Phe—COO— | or a C—C single bond, X is halogen, preferably chlorine, or —CN, and $R^6$ and $R^7$ are alkyl, alkoxy, alkanoyloxy or alkoxycarbonyloxy having up to 18, preferably up to 8, carbon atoms, or one of these radicals also is CN, NC, NO$_2$, CF$_3$, F, Cl or Br.

In most of these compounds, $R^6$ and $R^7$ differ from each other, one of these radicals usually being an alkyl or alkoxy group. However, other combinations of the substituents proposed are also common. Many such substances or mixtures thereof commercially available.

Dielectrics according to this invention contain about 0.1 to 60, preferably 5 to 40, % of one or more compounds of formula I.

Dielectrics of this invention are prepared in a conventional manner. As a rule, the components are dissolved in one another, preferably at elevated temperatures.

Liquid crystalline dielectrics according to the invention can be modified by suitable additives in such a way that they can be used in any type of liquid crystal display element hitherto disclosed.

Such additives are known to those skilled in the art, and are extensively described in the literature. Examples of what can be added include conducting salts, preferably ethyldimethyldodecylammonium 4-hexyloxybenzoate, tetrabutylammonium tetraphenylboronate and complex salts of crown ethers (compare, for example, I. Haller et al., Mol. Crystl. Liq. Cryst. volume 24, pages 249–258 (1973)), to improve the conductivity, dichroic dyestuffs for preparing colored guest-host systems, and substances to alter the dielectric anisotropy, the viscosity and/or the orientation of the nematic phases. Such substances are described, for example, in German Offenlegungsschriften 2,209,127, 2,240,864, 2,321,632, 2,338,281, 2,450,088, 2,637,430, 2,853,728 and 2,902,177, all of whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the meling point and c.p. is the clear point of a liquid crystal substance.

EXAMPLE 1

A solution of 5 g of 1-(4-methoxycarbonylcyclohexen-1-yl)-4-pentylpiperidine (b.p. 171°/0.4 mm Hg, obtainable from methyl cyclohexanone-4-carboxylate and 4-pentylpiperidine in toluene in the presence of p-toluenesulfonic acid) in 50 ml of THF is hydrogenated under 2 bar of H$_2$ using 0.5 g of 10% Pd-C; the catalyst is filtered off; and the filtrate is evaporated to dryness to give 1-(trans-4-methoxycarbonylcyclohexyl)4-pentylpiperidine, m.p. 5°, b.p. 177°/0.27 mbar.

The following compounds are obtained in a similar manner by hydrogenating the corresponding enamines:

1-cyclohexyl-4-pentylpiperidine
1-(trans-4-methylcyclohexyl)-4-pentylpiperidine
1-(trans-4-propylcyclohexyl)-4-propylpiperidine
1-(trans-4-propylcyclohexyl)-4-butylpiperidine
1-(trans-4-propylcyclohexyl)-4-pentylpiperidine
1-(trans-4-butylcyclohexyl)-4-propylpiperidine
1-(trans-4-butylcyclohexyl)-4-butylpiperidine
1-(trans-4-butylcyclohexyl)-4-pentylpiperidine
1-(trans-4-pentylcyclohexyl)-4-propylpiperidine
1-(trans-4-pentylcyclohexyl)-4-butylpiperidine
1-(trans-4-pentylcyclohexyl)-4-pentylpiperidine
1-(trans-4-decylcylohexyl)-4-pentylpiperidine
1-(trans-4-methoxycyclohexyl)-4-pentylpiperidine
1-(trans-4-propoxycyclohexyl)-4-propylpiperidine
1-(trans-4-propoxycyclohexyl)-4-butylpiperidine
1-(trans-4-propoxycyclohexyl)-4-pentylpiperidine
1-(trans-4-butoxycylohexyl)-4-propylpiperidine
1-(trans-4-butoxycyclohexyl)-4-butylpiperidine
1-(trans-4-butoxycyclohexyl)-4-pentylpiperidine
1-(trans-4-pentoxycyclohexyl)-4-propylpiperidine
1-(trans-4-pentoxycyclohexyl)-4-butylpiperidine
1-(trans-4-pentoxycyclohexyl)-4-pentylpiperidine
1-(trans-4-decoxycyclohexyl)-4-pentylpiperidine
1-(trans-4-methoxycarbonylcyclohexyl)-4-propylpiperidine
1-(trans-4-methoxycarbonylcyclohexyl)-4-butylpiperidine
1-(trans-4-ethoxycarbonylcyclohexyl)-4-propylpiperidine
1-(trans-4-ethoxycarbonylcyclohexyl)-4-butylpiperidine
1-(trans-4-ethoxycarbonylcyclohexyl)-4-pentylpiperidine
1-(trans-4-acetoxycyclohexyl)-4-propylpiperidine
1-(trans-4-acetoxycyclohexyl)-4-butylpiperidine
1-(trans-4-acetoxycyclohexyl)-4-pentylpiperidine
1-(trans-4-fluorocyclohexyl)-4-propylpiperidine
1-(trans-4-fluorocyclohexyl)-4-butylpiperidine
1-(trans-4-fluorocyclohexyl)-4-pentylpiperidine
1-(trans-4-chlorocyclohexyl)-4-pentylpiperidine
1-(trans-4-bromocyclohexyl)-4-pentylpiperidine
1-(trans-4-(trans-4-propylcyclohexyl)-cyclohexyl)-4-propylpiperidine
1-(trans-4-(trans-4-propylcyclohexyl)-cyclohexyl)-4-butylpiperidine
1-(trans-4-(trans-4-propylcyclohexyl)-cyclohexyl)-4-pentylpiperidine
1-(trans-4-(trans-4-butylcyclohexyl)-cyclohexyl)-4-propylpiperidine
1-(trans-4-trans-4-butylcyclohexyl)-cyclohexyl)-4-butylpiperidine
1-(trans-4-(trans-4-butylcyclohexyl)-cyclohexyl)-4-pentylpiperidine
1-(trans-4-(trans-4-pentylcyclohexyl)-cyclohexyl)-4-propylpiperidine
1-(trans-4-(trans-4-pentylcyclohexyl)-cyclohexyl)-4-butylpiperidine
1-(trans-4-(trans-4-pentylcyclohexyl)-cyclohexyl)-4-pentylpiperidine
1-(trans-4-methoxyphenylcyclohexyl)-4-propylpiperidine 1-(trans-4-p-methoxyphenylcyclohexyl)-4-butylpiperidine
1-(trans-4-p-methoxyphenylcyclohexyl)-4-pentylpiperidine
1-(trans-4-propylcyclohexyl)-4-p-cyanophenylpiperidine
1-(trans-4-butylcyclohexyl)-4-p-cyanophenylpiperidine
1-(trans-4-pentylcyclohexyl)-4-p-cyanophenylpiperidine.

EXAMPLE 2

2.49 g of 1-(4-carboxycyclohexyl)-4-pentylpiperidine (m.p. 208°) is boiled for 1 hour together with 2.4 g of SOCl$_2$; the mixture is evaporated to dryness; the crude acid chloride obtained is dissolved in 15 ml of toluene; 1 ml of pyridine and 1.42 g of 4-propylcyclohexanol are added; and the mixture is boiled for 2 hours. Water is then added. The phases are separated, and the organic phase is washed with water, dried over Na$_2$SO$_4$ and evaporated to dryness, to give 1-[trans-4-(trans-4-propylcyclohexyloxycarbonyl)-cyclohexyl]-4-pentylpiperidine.

The following compounds are obtained in a similar manner by esterification:
1-[trans-4-(p-tolyloxycarbonyl)-cyclohexyl]-4-pentylpiperidine
1-[trans-4-(p-propylphenyloxycarbonyl)-cyclohexyl]-4-propylpiperidine
1-[trans-(trans-4-butylcyclohexyloxycarbonyl)-cyclohexyl]-4-pentylpiperidine
1-(trans-4-p-fluorobenzoyloxycyclohexyl)-4-pentylpiperidine
1-(trans-4-p-cyanobenzoyloxycyclohexyl)-4-pentylpiperidine
1-[trans-4-(trans-4-propylcyclohexanecarbonyloxy)-cyclohexyl]-4-heptylpiperidine
1-(trans-4-propylcyclohexyl)-4-(p-fluorophenoxycarbonyl)piperidine
1-(trans-4-pentylcyclohexyl)-4-(p-cyanophenoxycarbonyl)piperidine
1-(trans-4-ethylcyclohexyl)-4-(trans-4-pentylcyclohexoxycarbonyl)-piperidine
1-(trans-4-butylcyclohexyl)-4-(p-fluorobenzoyloxy)-piperidine
1-(trans-4-butylcyclohexyl)-4-(p-cyanobenzoyloxy)-piperidine
1-(trans-4-pentylcyclohexyl)-4-(trans-4-propylcyclohexanecarbonyloxy)-piperidine.

EXAMPLE 3

A solution of 100 mg of 1-(4-carbamoylcyclohexyl)-4-pentylpiperidine [m.p. 186°; obtainable by hydrolyzing 1-(trans-4-methoxycarbonylcyclohexyl)-4-pentylpiperidine with methanolic KOH to give the carboxylic acid (m.p. 208°), converting the acid into the acid chloride with SOCl$_2$, and reacting it with aqueous NH$_3$ solution]and 1 ml of POCl$_3$ are stirred at 20° for 15 hours in 5 ml of pyridine; the mixture is evaporated to dryness; and the 1-(trans-4-cyanocyclohexyl)-4-pentylpiperidine hydrochloride is recrystallized from ethyl acetate; m.p. 260° (decomposition). Free base, m.p. 56.6°, c.p. 64.8°.

The following compounds are obtained in a similar manner by dehydrating the corresponding amides:
1-(trans-4-cyanocyclohexyl)-4-fluoropiperidine
1-(trans-4-cyanocyclohexyl)-4-methylpiperidine
1-(trans-4-cyanocyclohexyl)-4-ethylpiperidine
1-(trans-4-cyanocyclohexyl)-4-propylpiperidine
1-(trans-4-cyanocyclohexyl)-4-butylpiperidine
1-(trans-4-cyanocyclohexyl)-4-hexylpiperidine
1-(trans-4-cyanocyclohexyl)-4-heptylpiperidine
1-(trans-4-cyanocyclohexyl)-4-octylpiperidine
1-(trans-4-cyanocyclohexyl)-4-nonylpiperidine
1-(trans-4-cyanocyclohexyl)-4-decylpiperidine
1-(trans-4-cyanocyclohexyl)-4-methoxypiperidine
1-(trans-4-cyanocyclohexyl)-4-ethoxypiperidine
1-(trans-4-cyanocyclohexyl)-4-propoxypiperidine
1-(trans-4-cyanocyclohexyl)-4-butoxypiperidine
1-(trans-4-cyanocyclohexyl)-4-pentoxypiperidine
1-(trans-4-cyanocyclohexyl)-4-decoxypiperidine.

EXAMPLE 4

A mixture of 2.29 g of 1-dimethoxymethyl-4-pentylpiperidine (obtainable by formylating 4-pentylpiperidine and then reacting with dimethyl sulfate and Na methylate/methanol), 1.46 g of 2-pentylpropane1,3-diol, 0.01 g of p-toluenesulfonic acid and 20 ml of toluene is boiled for 3 hours, during which the methanol formed is distilled off, and the mixture is cooled down, washed with water and evaporated. This gives 2-(4-pentyl-1-piperidyl)-5-pentyl-1,3-dioxane, m.p. 46°-51°.

The following compounds are obtained in a similar manner by reacting the corresponding 1-dimethoxymethylpiperidines with the corresponding diols:
2-(4-propyl-1-piperidyl)-5-propyl-1,3-dioxane
2-(4-butyl-1-piperidyl)-5-propyl-1,3-dioxane
2-(4-pentyl-1-piperidyl)-5-propyl-1,3-dioxane
2-(4-propyl-1-piperidyl)-5-butyl-1,3-dioxane
2-(4-butyl-1-piperidyl)-5-butyl-1,3-dioxane
2-(4-pentyl-1-piperidyl)-5-butyl-1,3-dioxane
2-(4-propyl-1-piperidyl)-5-pentyl-1,3-dioxane
2-(4-butyl-1-piperidyl)-5-pentyl-1,3-dioxane.

EXAMPLE 5

A mixture of 1 g of hexanal, 2.29 g of 1-(1,3-dihydroxy-2-propyl)-4-pentylpiperidine [obtainable by reacting diethyl bromomalonate with 4-pentylpiperidine to give 1-bis-(ethoxycarbonyl)-methyl-4-pentylpiperidine, which is then reduced with LiALH$_4$], 0.01 g of p-toluenesulfonic acid and 15 ml of toluene is boiled for 3 hours under a water separator, and the mixture is cooled down, washed with water and evaporated. This gives 2-pentyl-5-(4-pentyl-1-piperidyl)-1,3-dioxane.

The following compounds are obtained in a similar manner by reacting the corresponding aldehydes with the corresponding diols:
2-propyl-5-(4-propyl-1-piperidyl)-1,3-dioxane
2-butyl-5-(4-propyl-1-piperidyl)-1,3-dioxane
2-pentyl-5-(4-propyl-1-piperidyl)-1,3-dioxane
2-propyl-5-(4-butyl-1-piperidyl)-1,3-dioxane
2-butyl-5-(4-butyl-1-piperidyl)-1,3-dioxane
2-pentyl-5-(4-butyl-1-piperidyl)-1,3-dioxane
2-propyl-5-(4-pentyl-1-piperidyl)-1,3-dioxane
2-butyl-5-(4-pentyl-1-piperidyl)-1,3-dioxane.

Examples of dielectrics according to the invention follow. These contain at least one compound of formula I:

EXAMPLE A

A mixture of
23% of 1-(trans-4-cyanocyclohexyl)-4-pentylpiperidine
28% of trans,trans-4-ethylcyclohexylcyclohexane-4'-carbonitrile
19% of trans,trans-4-propylcyclohexylcyclohexane-4'-carbonitrile, and 30% of trans,trans-4-heptylcyclohexylcyclohexane-4'-carbonitrile has an m.p. of 3° and a c.p. of 68°.

EXAMPLE B

A mixture of

15% of 1-(trans-4-cyanocyclohexyl)-4-propylpiperidine
15% of 1-(trans-4-cyanocyclohexyl)-4-pentylpiperidine
20% of trans,trans-4-butylcyclohexylcyclohexane-4'-carbonitrile
18% of trans-1-p-ethoxyphenyl-4-propylcyclohexane
15% of p-(trans-4-propylcyclohexyl)-benzonitrile
7% of trans-4-propylcyclohexyl trans,trans-4-butylcyclohexylcyclohexane-4'-carboxylate, and
10% of p-(trans-4-propylcyclohexyl)-phentyl trans-4-pentylcyclohexanecarboxylate has an m.p. of −7° and a c.p. of 57°.

EXAMPLE C

A mixture of

15% of 1-(trans-4-cyanocyclohexyl)-4-propylpiperidine
15% of 1-(trans-4-cyanocylohexyl)-4-pentylpiperidine
25% of trans,trans-4-pentylcyclohexylcyclohexane-4'-carbonitrile
25% of trans,trans-4-heptylcyclohexylcyclohexane-4'-carbonitrile
10% of trans-1-p-butoxyphenyl-4-propylcyclohexane
8% of 4,4'-bis-(trans-4-pentylcyclohexyl)-biphenyl, and
2% of 1,5-diamino-4,8-dihydroxy-3-p-methoxyphenylanthraquinone has a c.p. of 82°.

The preceding examples can be repeated with similar success by substituting the generically or specifically described reactants and/or operating conditions of this invention for those used in the preceding Examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid crystalline dielectric material useful in electro-optical display elements and comprising at least two liquid crystalline components, wherein at least one component is a piperidine derivative of the formula

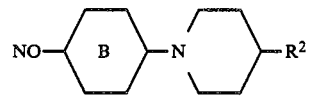

wherein
R$^2$ is alkyl or alkoxy each of 1 to 10 carbon atoms, F, CL or Br or an acid addition salt thereof.

2. A dielectric of claim 1 containing 1,4-cyclohexylene groups having substituents in the trans-position relative to each other.

3. A dielectric of claim 1 containing alkyl or alkoxy groups all of which are straight-chained.

4. A dielectric of claim 1 wherein the alkyl and alkoxy groups are of 2-6 C atoms.

5. A dielectric of claim 1 wherein R$^2$ is straight-chain alkyl of 2-6 C atoms.

6. A dielectric of claim 1 wherein R$^2$ is alkyl.

7. A dielectric of claim 1 comprising 2-15 liquid crystalline components.

8. A dielectric of claim 1 comprising 0.1-60 wt % of said piperidine component.

9. A dielectric of claim 1 comprising 5-40 wt % of said piperidine component.

10. In an electro-optical display element, comprising a liquid crystalline dielectric, the improvement wherein the dielectric is that of claim 1.

* * * * *

UNITED STATES PATENT AND TRADEMARK OFFICE
CERTIFICATE OF CORRECTION

PATENT NO. : 4,537,698
DATED : August 27, 1985
INVENTOR(S) : WOLFGANG SUCROW ET AL It is certified that error appears in the above-identified patent and that said Letters Patent is hereby corrected as shown below:

The formula in claim 1 should read --

--.

Signed and Sealed this

Fourth Day of March 1986

[SEAL]

Attest:

DONALD J. QUIGG

Attesting Officer     Commissioner of Patents and Trademarks